(12) United States Patent
Nakamura

(10) Patent No.: US 6,468,555 B1
(45) Date of Patent: Oct. 22, 2002

(54) PESTICIDAL COMPOSITIONS

(75) Inventor: Satoshi Nakamura, Mino (JP)

(73) Assignee: Sumitomo Chemical Company, Limited, Osaka (JP)

(*) Notice: Subject to any disclaimer, the term of this patent is extended or adjusted under 35 U.S.C. 154(b) by 0 days.

(21) Appl. No.: 09/544,212

(22) Filed: Apr. 7, 2000

(30) Foreign Application Priority Data

Apr. 14, 1999 (JP) .............................. 11/106794

(51) Int. Cl.[7] .............................. A01N 25/32
(52) U.S. Cl. .................. 424/406; 424/405; 514/345; 514/374
(58) Field of Search .................. 424/405; 514/345, 514/374

(56) References Cited

U.S. PATENT DOCUMENTS

| 4,751,225 A | | 6/1988 | Nishida et al. | |
|---|---|---|---|---|
| 5,466,703 A | | 11/1995 | Kudoh et al. | |
| 6,001,829 A | * | 12/1999 | Kramer et al. | 574/236.2 |
| 6,093,415 A | * | 7/2000 | Karr et al. | 424/406 |

FOREIGN PATENT DOCUMENTS

WO        WO9322297        11/1993

* cited by examiner

Primary Examiner—Neil S. Levy
(74) Attorney, Agent, or Firm—Birch, Stewart, Kolasch & Birch, LLP.

(57) ABSTRACT

Pesticidal compositions containing 4-phenoxyphenyl 2-(2-pyridyloxy)propyl ether and 2-(2,6-difluorophenyl)-4-(2-ethoxy-4-tert-butyl-phenyl)-2-oxazoline as active ingredients have excellent pesticidal efficacy.

7 Claims, No Drawings

PESTICIDAL COMPOSITIONS

FILED OF INVENTION

The present invention relates to pesticidal compositions.

BACKGROUND OF THE INVENTION

The development of pesticides has been widely carried out for the control of many kinds of pests including agricultural and forest pests and hygienically unfavorable pests, and a wide variety of chemical agents have been put to practical use. All conventional pesticides, however, cannot be said to give satisfactory results; for example, they may lack at least one of lethal efficacy, immediate effect, and residual effect, or they may have poor results on the specific kinds of pests or on the specific growth stage of pests. Accordingly, there has been a demand for the development of more excellent pesticides.

SUMMARY OF THE INVENTION

Under these circumstances, the present inventors have concentrated on the study and consequently found that pesticidal compositions comprising 4-phenoxyphenyl 2-(2-pyridyloxy)propyl ether and 2-(2,6-difluorophenyl)-4-(2-ethoxy-4-tert-butyl-phenyl)-2-oxazoline as active ingredients, when used to control agricultural and forest pests or hygienically unfavorable pests, can have unpredictably high pesticidal efficacy and exhibit excellent immediate effect and residual effect as compared with the separate application of each compound, making it possible to solve the above problems, which leads to the present invention.

Thus the present invention provides pesticidal compositions (hereinafter referred to as the present compositions) comprising 4-phenoxyphenyl 2-(2-pyridyloxy)propyl ether (hereinafter referred to as compound A) and 2-(2,6-difluorophenyl)-4-(2-ethoxy-4-tert-butyl-phenyl)-2-oxazoline (hereinafter referred to as compound B) as active ingredients; pest control methods comprising application of the present compositions to pests or their habitats; and plant protection methods comprising application of the present compositions to plants or their neighborhood, which may be infested with agricultural and forest pests.

DETAILED DESCRIPTION OF THE INVENTION

The active ingredients in the present compositions are well known in the art; compound A (common name: pyriproxyfen) from U.S. Pat. No. 4,751,225 and compound B (common name: etoxazole) from WO 93/22297.

The present compositions can be applied as control agents against many kinds of pests including agricultural and forest pests and hygienically unfavorable pests. Specific examples of the pests which can be controlled by the present compositions are the following insects, acarines, and nematodes.

Hemiptera

Delphacidae such as *Laodelphax striatellus, Nilaparvata lugens*, and *Sogatella furcifera*; Deltocephalidae such as *Nephotettix cincticeps* and *Nephotettix virescens*; Aphididae such as *Aphis gossypii, Myzus persicae, Aphis citricola, Lipaphis pserudobrassicae, Nippolachnus piri, Toxoptera aurantii*, and *Toxoptera ciidius*; Pentatomidae such as *Nezara antennata, Cletus punctiger, Riptortus clavetus*, and *Plautia stali*; Aleyrodidae such as *Trialeurodes vaporariorum, Bemisia tabaci*, and *Bemisia argentifolii*; Diaspididae such as *Aonidiella aurantii, Comstockaspis perniciosa, Unaspis citri, Pseudaulacaspis pentagons*, and *Lepidosaphes beckii*; Coccidae such as *Saissetia oleae* and *Ceroplastes rubens*; Margarodidae such as *Icerya purchasi*; Tingidae; Psyllidae, etc.

Lepidoptera

Pyralidae such as *Chilo suppressalis, Cnaphalocrocis medinalis, Ostrinia nubilalis, Parapediasia teterrella, Notarcha derogata*, and *Plodia interpunctella*; Noctuidae such as *Spodoptera litura, Pseudaletia separata, Mamestra brassicae, Agrotis ipsilon*, Trichoplusia spp., Heliothis spp., and Helicoverpa spp.; Pieridae such as *Pieris rapae crucivora*; Tortricidae such as Adoxophyes spp., *Grapholita molesta*, and *Cydia pomonella*; Carposinidae such as *Carposina niponensis*; Lyonetiidae such as Lyonetia spp.; Lymantriidae such as Lymantria spp. and Euproctis spp.; Yponomeutidae such as *Plutella xylostella*; Gelechiidae such as *Pectinophora gossypiella*; Arctiidae such as *Hyphantria cunea*; Tineidae such as *Tinea translucens* and *Tineola bisselliella*, etc.

Diptera

Calicidae such as *Culex pipiens pallens* and *Culex tritaeniorhynchus*; Aedes spp. such as *Aedes aegypti* and *Aedes albopictus*; Anopheles spp. such as *Anopheles sinensis*; Chironomidae; Muscidae such as *Musca domestica* and *Muscina stabulans*; Calliphoridae; Sarcophagidae; Finnia spp.; Anthomyiidae such as *Delia platura* and *Delia antiqua*; Tephritidae; Drosophilidae; Psychodidae; Simuliidae; Tabanidae; Stomoxyinae; Agromyzidae, etc.

Coleoptera

Diabrotica spp. such as *Diabrotica virgifera virgifera* and *Diabrotica undecimpunctata howardi*; Scarabaeidae such as *Anomala cuprea* and *Anomala rufocuprea*; Curculionidae such as *Sitophilus zeamais, Lissorhoptrus oryzophilus, Hypera pastica*, and *Callosobruchuys chienensis*; Tenebrionidae such as *Tenebrio molitor* and *Tribolium castaneum*; Chrysomelidae such as *Aulacophora femoralis, Phyllotreta striolata*, and *Leptinotarsa decemlineata*; Anobiidae; Epilachna spp. such as *Epilachna vigintioctopunctata*; Lyctidae; Bostrychidae; Cerambycidae; *Paederus fuscipes*, etc.

Dictyoptera

*Blattella germanica, Periplaneta fuliginosa, Periplaneta americana, Periplaneta brunnea, Blatta orientalis*, etc.

Thysanoptera

*Thrips palmi, Thrips tabaci, Thrips hawaiiensis, Scirtothrips dorsalis, Frankliniella intonsa, Frankliniella occidentalis, Ponticulothrips diospyrosi*, etc.

Hymenoptera

Formicidae, Vespidae, Bethylidae, Tenthredinidae such as *Athalia japonica*, etc.

Orthoptera

Gryllotalpidae, Acrididae, etc.

Aphaniptera

*Ctenocephalides felis, Ctenocephalides canis, Purex irritans*, etc.

Anoplura

*Pediculus humanus corporis, Phthirus pubis*, etc.

Isoptera

*Reticulitermes speratus, Coptotermes formosanus*, etc.

Acarina

Tetranychidae such as *Tetranychus urticae, Tetranychus kanzawai, Panonychus citri, Panonychus ulmi*, and Oligonychus spp.; Eriophyidae such as *Aculops pelekassi* and *Calacarus carinatus*, Tarsonemidae such as *Polyphagotarsonemus latus*; Tenuipalpidae; Tuckerellidae; Ixodidae such as *Haemaphysalis japonica, Haemaphysalis flava, Haemaphysalis Longicornis, Boophilus microplus, Ixodes ovatus*, and *Ixodes persulcatus*; Acaridae such as *Tyrophagus putresceutiae*; Epidermoptidae such as *Dermatophagoides farinae* and *Dermatophagoides ptrenyssnus*; Cheyletidae such as *Cheyletus eruditus, Cheyletus fortis, Cheyletus malaccensis*, and *Cheyletus moorei*; Dermanyssidae, etc.

Nematoda

*Pratylenchus coffeae, Pratylenchus fallax, Pratylenchus loosi, Pratylenchus vulnus, Heterodera glycines, Globodera rostochiensis, Meloidogyne hapla, Meloidogyne incognita*, etc.

The present compositions, although they may consist of compound A and compound B, can be made suitable for practical use by allowing various solid, liquid, or gaseous carriers to hold the present compositions, to which surfactants, dispersants, fixing agents, stabilizers, propellants, or other auxiliaries are added, if necessary, followed by formulation into various forms including oil sprays, emulsifiable concentrates, wettable powders, flowables such as aqueous suspensions and aqueous emulsions, microcapsule formulations, spot-on or pour-on formulations, shampoo formulations, granules, dusts, aerosols, ULV agents, poison baits, sheet-shaped formulations, and resin formulations.

The solid carrier which can be used in the formulation may include, for example, fine powder or granules of clay materials such as kaolin clay, diatomaceous earth, synthetic hydrated silicon oxide, bentonite, Fubasami clay, and acid clay; various kinds of talc, ceramics, and other inorganic minerals such as sericite, quartz, sulfur, activated carbon, calcium carbonate, and hydrated silica; and chemical fertilizers such as ammonium sulfate, ammonium phosphate, ammonium nitrate, urea, and ammonium chloride.

The liquid carrier may include, for example, water; alcohols such as methanol and ethanol; ketones such as acetone and methyl ethyl ketone; aromatic hydrocarbons such as benzene, toluene, xylene, ethylbenzene, and methylnaphthalene; aliphatic hydrocarbons such as hexane, cyclohexane, kerosene, and light oil; esters such as ethyl acetate and butyl acetate; nitrites such as acetonitrile and isobutyronitrile; ethers such as diisopropyl ether and dioxane; acid amides such as N,N-dimethylformamide and N,N-dimethylacetamide; halogenated hydrocarbons such as dichloromethane, trichloroethane, and carbon tetrachloride; dimethyl sulfoxide; and vegetable oils such as soybean oil and cottonseed oil.

The gaseous carrier or propellant may include, for example, fluoro-carbons, butane gas, LPG (liquefied petroleum gas), dimethyl ether, and carbon dioxide.

The surfactant may include, for example, alkylsulfates, alkylsulfonates, alkylarylsulfonates, alkyl aryl ethers and their polyoxyethylene derivatives, polyethylene glycol ethers, polyhydric alcohol esters, and sugar alcohol derivatives.

The auxiliaries such as fixing agents or dispersants may include, for example, casein, gelatin, polysaccharides such as starch, arabic gum, cellulose derivatives, and alginic acid; lignin derivatives, bentonite, sugars, and synthetic water-soluble polymers such as polyvinyl alcohol, polyvinyl pyrrolidone, and polyacrylic acid.

The stabilizer may include, for example, PAP (isopropyl acid phosphate), BHT (2,6-di-tert-butyl-4-methylphenol), BHA (mixtures of 2-tert-butyl-4-methoxyphenol and 3-tert-butyl-4-methoxyphenol), vegetable oils, mineral oils, surfactants, fatty acids and their esters.

The base materials of poison baits may include, for example, bait ingredients such as grain powder, vegetable oils, sugars, and crystalline cellulose; antioxidants such as dibutylhydroxytoluene and nordihydro-guaiaretic acid; preservatives such as dehydroacetic acid; substances for preventing erroneous eating, such as red pepper powder; and attractants such as cheese flavor, onion flavor, and peanut oil.

The base materials of resin formulations may include, for example, olefin polymers, vinyl chloride polymers, and polyurethanes. To these base materials, there can be added, if necessary, plasticizers such as phthalates and stearic acid; pest-attractive substances such as pheromones; dyes or pigments with pest-attractive colors; and any other additives.

The resin formulations can be obtained, for example, by kneading the present compositions into the base materials with a conventional kneader and then forming into a desired shape by injection, extrusion, or compression molding. The present compositions may be supported on the base materials which do not contain them, by impregnation, coating, printing, or any other techniques. In the operation, for example, impregnation, coating, or printing of the present compositions, compounds as the active ingredients may be used in the form of previously-prepared formulations or their dilutions, including oil sprays, emulsifiable concentrates, and flowables.

The resin formulations thus obtained can be formed through further steps, if necessary, such as shaping and cutting, into plates, sheets or films, tapes or ribbons, nets, strings or cords, or any other shapes, and can also be formed into final products such as materials for mulching, strings or cords for training, supports for horticultural use, sheet-shaped formulations, films for wrapping use, collars for animals, and ear tags for animals.

The formulations as flowables (e.g., aqueous suspensions or aqueous emulsions) can usually be obtained by finely dispersing 1–75% active ingredients in water containing 0.5–15% dispersants, 0.1–10% suspension aids (e.g., protective colloids, thixotropy-conferring compounds), and 0–10% suitable auxiliaries (e.g, antifoaming agents, rust preventives, stabilizers, spreading agents, penetration aids, antifreezing agents, antiblastic agents, antifungal agents). The replacement of water with oils in which the active ingredients can hardly be dissolved makes it possible to produce oily suspensions.

As the protective colloids, there can be used, for example, gelatin, casein, various kinds of gum, cellulose ethers, polyvinyl alcohol, or other similar materials. The thixotropy-conferring compounds may include, for example, bentonite, aluminum magnesium silicate, xanthan gum, and polyacrylic acid.

The mixing ratios of compound A and compound B in the present compositions are not strictly limited, but they can be changed over a wide range depending upon types of formulations, uses, and other factors. The mixing ratios are usually in the range of 0.01 to 30 parts, preferably 0.5 to 10 parts, of compound B for 1 part of compound A, and the total amounts of compound A and compound B contained in the present compositions are usually in the range of 0.01% to 90% by weight, preferably 0.1% to 80% by weight.

The present compositions can also be used in admixture or together with other insecticides, nematocides, acaricides, bactericides, fungicides, herbicides, plant growth regulators, synergists, fertilizers, soil conditioners and/or feeds for animals. The insecticides, acaricides, and nematocides may include, for example, pyrethroid compounds such as permethrin, cypermethrin, fenvalerate, esfenvalerate, fenpropathrin, bifenthrin, deltamethrin, fluvalinate, flucythrinate, allethrin, d-allethrin, prallethrin, cyphenothrin, phenothrin, resmethrin, tefluthrin, empenthrin, acrinathrin, cyhalothrin, cyfluthrin, etofenprox, halfenprox, silafluofen, tralomethrin, cycloprothrin, esbiothrin, transfluthrin, terallethrin, imiprothrin, and 1-ethynyl-2-fluoro-2-pentenyl 3-(2,2-dichlorovinyl)-2,2-dimethylcyclopropanecarboxylate; organo-phosphorus compounds such as cyanophos, fenthion, fenitrothion, parathion, methyl parathion, pirimiphos-methyl, diazinon, isoxathion, pyridaphenthion, chlorpyriphos, chlorpyriphos-methyl, oxydeprofos, vamidothion, malathion, phenthoate, dimethoate, thiometon, disulfoton, phosalone, phosmet, methidathion, prothiofos, sulprofos, profenofos, azinphos-methyl, pyraclofos, salithion, tetrachlorvinphos, dichlorvos, monocrotophos, naled, dimethylvinphos, propaphos, acephate, methamidophos, and ethion; carbamate compounds such as carbaryl, metolcarb, isoprocarb, fenobucarb, propoxur, XMC, ethiofencarb, bendiocarb, pirimicarb, carbosulfan, carbofuran, benfuracarb, furathiocarb, methomyl, thiodicarb, oxamyl, alanycarb, metoxadiazone, and fenothiocarb; neo-nicotinoids including nitroiminoimidazolidine derivatives, nitrovinylidenediamine derivatives such as N-(6-chloro-3-pyridylmethyl)-N-ethyl-N'-methyl-2-nitrovinylidenediamine (common name: nitenpyram), nitroguanidine derivatives such as 1-methyl-2-nitro-3-[(3-tetrahydrofuryl)-methyl]guanidine, cyanoacetoamidine derivatives such as $N^1$-[(6-chloro-3-pyridyl)methyl]-$N^2$-cyano-$N^1$-methylacetoamidine (common name: acetamiprid), cyanoiminothiazoline derivatives such as 1-(2-chloro-5-pyridylmethyl)-2-cyanoiminothiazoline (common name: thiacloprid), nitroiminotetrahydro-1,3,5-oxadiadine derivatives such as 3-[(2-chloro-5-thiazolyl)methyl]-5-methyl-4-nitroiminotetrahydro-1,3,5-oxadiadine (common name: thiamethoxam), and nitroiminohexahydro-1,3,5-triazine derivatives such as 3,5-dimethyl-1-[(2-chloro-5-thiazolyl)methyl]-2-nitroiminohexahydro-1,3,5-triazine; nereistoxin derivatives such as cartap, bensultap, and thiocyclam; chlorinated hydrocarbon compounds such as benzoepin, dicofol, and tetradifon; formamidine derivatives such as amitraz and chlordimeform; phenylpyrazole derivatives such as ethiprole; benzoylphenyl urea compounds such as diflubenzuron, teflubenzuron, chlorfluazuron, flufenoxuron, triflumuron, hexaflumuron, lufenuron, and novaluron; triazine derivatives such as cyromazine; thiadiazine derivatives such as buprofezin; juvenoid compounds such as methoprene, hydroprene, fenoxycarb, and diofenolan; tebufenozide, methoxyfenozide, halofenozide, chromafenozide, chlorfenapyr, phenisobromolate, chinomethionat, propargite, fenbutatin oxide, hexythiazox, clofentezine, pyridaben, fenpyroximate, tebufenpyrad, pyrimidifen, polynactin, milbemectin, avermectin, ivermectin, and azadirachtin.

When the present compositions are applied for use in the control of agricultural and forest pests, their amounts for application are usually in the range of 1 g to 1000 g, preferably 10 g to 100 g, per 10 ares in terms of the total amounts of active ingredients. For emulsifiable concentrates, wettable powders, flowables, or other similar formulations, which are used after dilution with water, their concentrations for application are usually in the range of 10 ppm to 1000 ppm in terms of the total amounts of active ingredients. In contrast, granules, dusts, or other similar formulations are applied as such. These formulations may be sprayed over the foliage of plants such as crop plants to be protected from pests or may be used in the soil treatment for the control of pests inhabiting the soil. The present compositions may also be formed into sheet-shaped, or string- or cord-shaped formulations, which are applied by directly winding around plants, disposing in the neighborhood of plants, or spreading on the soil surface at the root.

When the present compositions are applied for use in the control of hygienically unfavorable pests, emulsifiable concentrates, wettable powders, flowables, or other similar formulations are usually applied after dilution with water to the total amounts of active ingredients ranging from 0.01 ppm to 10,000 ppm, and oil sprays, aerosols, smoke formulations, ULV agents, poison baits, or other similar formulations are applied as such. When the present compositions are used in the direct treatment of animal bodies for the control of ectoparasites on small animals such as cats and dogs, they may be applied by the known veterinary methods: for example, as tablets, by feed incorporation, as suppositories, or by injection (intramuscular, subcutaneous, intravenous, intraperitoneal, or any other routes) for systemic control; or by spraying oily or aqueous solutions, by spot-on or pour-on treatment, or as shampoo formulations or resin formulations such as collars and ear tags for non-systemic control. For such direct application to animal bodies, the amounts for application are usually in the range of 0.1 mg to 500 mg per kg of a host animal in terms of the total amounts of active ingredients.

These amounts or concentrations for application may vary depending upon types of formulations, times, places, and methods of application, kinds of pests, degree of damage, and other factors; they can therefore be increased or decreased without limitation to the above ranges.

EXAMPLES

The present invention will be further illustrated by the following formulation examples and test examples; however, the present invention is not limited to these examples. Unless otherwise indicated, parts are by weight.

Formulation Example 1

Emulsifiable Concentrate

Five parts of compound A, 10 parts of compound B, 8 parts of polyoxyethylene alkyl aryl ether, 2 parts of sodium alkylarylsulfonate, and 75 parts of xylene are uniformly mixed to give an emulsifiable concentrate.

Formulation Example 2

Wettable Powder

Five parts of compound A, 10 parts of compound B, 3 parts of sodium alkylbenzenesulfonate, 3 parts of sodium ligninsulfonate, and 79 parts of diatomaceous earth are uniformly mixed and pulverized with a jet air mill.

Formulation Example 3

Dust

One part of compound A, 1 part of compound B, 48 parts of talc, and 50 parts of clay are uniformly mixed and pulverized to give a dust.

Formulation Example 4

Flowable

Five parts of polyoxyethylene styryl phenyl ether sulfate, 20 parts of 1% aqueous solution of xanthan gum, 3 parts of smectite-group mineral, and 57 parts of water are uniformly mixed, to which 5 parts of compound A and 10 parts of compound B are added, and the resultant mixture is well stirred and then wet pulverized in a sand mill to give a flowable.

Formulation Example 5

Microcapsule Formulation

Five parts of compound A, 5 parts of compound B, 10 parts of phenyl xylyl ethane, and 0.5 part of Sumidur L-75 (tolylene diisocyanate available from Sumitomo Bayer Urethane Co., Ltd.) are mixed, and the resultant mixture is then poured into 20 parts of 10% aqueous solution of arabic gum, followed by stirring in a homomixer to give an emulsion with an average particle diameter of 20 µm. To this is then added 2 parts of ethylene glycol, and the reaction is allowed to proceed in a water bath at 60° C. for 24 hours to give a microcapsule slurry. Separately, 0.2 part of xanthan gum and 1.0 part of Beegum R (aluminum magnesium silicate available from Sanyo Chemical Industries, Ltd.) are dispersed in 56.3 parts of ion-exchanged water to give a viscosity-improver solution.

Finally, 42.5 parts of the above microcapsule slurry and 57.5 parts of the above viscosity-improver solution are mixed to give a 10% microcapsule formulation.

Formulation Example 6

Oil Spray

First, 0.1 part of compound A and 0.1 part of compound B are dissolved in a mixture of 5 parts of xylene and 5 parts of trichloroethane, and the resultant solution is then mixed with 89.9 parts of deodorized kerosine to give an oil spray.

Formulation Example 7
Poison Bait

First, 5 mg of compound A and 5 mg of compound B are dissolved in 0.5 ml of acetone, and the resultant solution is then uniformly mixed with 5 g of solid feed powder for animals (Breeding Solid Feed Powder CE-2 available from Japan Clea Co., Ltd.). Air drying of the mixture to remove the acetone gives a poison bait.

Formulation Example 8
Resin Formulation

First, 1 part of compound A and 1 part of compound B are kneaded with 98 parts of polyethylene resin (Sumikathene available from Sumitomo Chemical Co., Ltd.) in a pressure kneader, followed by pelletizing. The pellets are extruded at 160° C. to 180° C. with an inflation film making machine to give a film-shaped resin formulation with a thickness of 0.1 mm.

Formulation Example 9
Heating Smoke Formulation

First, 50 mg of compound A and 50 mg of compound B are dissolved in a suitable amount of acetone. The resultant solution is then absorbed in a porous ceramic plate with a size of 4.0 cm×4.0 cm and a thickness of 1.2 cm to give a heating smoke formulation.

The following test examples are presented for demonstrating that the present compositions are useful as active ingredients of pesticides.

Test Example 1
Pesticidal Test Against *Aphis gossypii*

Twenty adults of *Aphis gossypii* were set free on three-leafed cabbage plants in pots. These plants were uniformly sprayed using a spray gun with a water dilution in a prescribed concentration of a commercial product of compound A (trade name: Lano 10EC; available from Sumitomo Chemical Co., Ltd.), a commercial product of compound B (trade name: Baroque Flowable; available from Yashima Chemical Industry Co., Ltd.), or a mixture of the commercial product of compound A and the commercial product of compound B. After air drying, the pots were placed in a greenhouse. On a predetermined day after the application, the cabbage plants were examined for the number of aphids surviving thereon. The results are shown in Table 1.

TABLE 1

| Test compound(s) | Amount of active ingredient(s) (ppm) | Number of surviving aphids per pot | |
|---|---|---|---|
| | | After 3 days | After 6 days |
| Compound A | 2.0 | 45 | 11 |
| Compound B | 2.0 | 11 | 25 |
| Compound A + Compound B | 2.0 + 2.0 | 4 | 0 |
| None | — | 31 | 48 |

Test Example 2
Pesticidal Test Against *Bemisia argentifolii*

Cabbage seedlings infested with first-instar nymphs of *Bemisia argentifollii* were uniformly sprayed using a spray gun with a water dilution in a prescribed concentration of a commercial product of compound A (trade name: Lano 10EC; available from Sumitomo Chemical Co., Ltd.), a commercial product of compound B (trade name: Baroque Flowable; available from Yashima Chemical Industry Co., Ltd.), or a mixture of the commercial product of compound A and the commercial product of compound B. After air drying, each of the cabbage seedlings was placed in a net cage and kept in a greenhouse. After 16 days from the application, the number of emergent adults was determined. The results are shown in Table 2.

TABLE 2

| Test compound(s) | Amount of active ingredient(s) (ppm) | Number of nymphs used in test | Number of emergent adults |
|---|---|---|---|
| Compound A | 0.2 | 108 | 13 |
| Compound B | 0.4 | 125 | 51 |
| Compound A + Compound B | 0.2 + 0.1 | 105 | 0 |
| | 0.2 + 0.2 | 115 | 3 |
| | 0.2 + 0.4 | 107 | 0 |
| None | — | 120 | 84 |

What is claimed is:

1. A pesticidal composition comprising a synergistically effective amount of 4-phenoxyphenyl 2-(2-pyridyloxy)propyl ether and 2-(2,6-difluorophenyl)-4-(2-ethoxy-4-tert-butylphenyl)-2-oxazoline as active ingredients.

2. The pesticidal composition according to claim 1, wherein the weight ratio of 4-phenoxyphenyl 2-(2-pyridyloxy)propyl ether and 2-(2,6-difluorophenyl)-4-(2-ethoxy-4-tert-butyl-phenyl)-2-oxazoline is in the range of 100:1 to 1:30.

3. A pest control method comprising application of a pesticidal composition according to claim 1 or 2 to pests or their habitats.

4. A plant protection method comprising application of a pesticidal composition according to claim 1 or 2 to plants or their neighborhood, which may be infested with agricultural and forest pests.

5. The pesticidal composition according to claim 1, wherein the weight ratio of 4-phenoxyphenyl 2-(2-pyridyloxy)propyl ether and 2-(2,6-difluorophenyl)-4-(2-ethoxy-4-tert-butylphenyl)-2-oxazoline is in the range of 1:0.5 to 1:10.

6. The pesticidal composition according to claim 1, wherein the weight ratio of 4-phenoxyphenyl 2-(2-pyridyloxy)propyl ether and 2-(2,6-difluorophenyl)-4-(2-ethoxy-4-tert-butylphenyl)-2-oxazoline is in the range of 1:2 to 2:1.

7. The pesticidal composition according to claim 1, wherein the weight ratio of 4-phenoxyphenyl 2-(2-pyridyloxy)propyl ether and 2-(2,6-difluorophenyl)-4-(2-ethoxy-4-tert-butylphenyl)-2-oxazoline is in the range of 1:10 to 10:1.

* * * * *